(12) United States Patent  
Wahrenberg

(10) Patent No.: US 9,468,420 B2  
(45) Date of Patent: Oct. 18, 2016

(54) MEDICAL IMAGING DATA PROCESSING APPARATUS AND METHOD

(71) Applicant: Toshiba Medical Systems Corporation, Otawara-shi (JP)

(72) Inventor: Magnus Wahrenberg, Edinburgh (GB)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/875,565

(22) Filed: May 2, 2013

(65) Prior Publication Data

US 2014/0328526 A1   Nov. 6, 2014

(51) Int. Cl.  
*A61B 8/00*   (2006.01)  
*A61B 8/08*   (2006.01)

(52) U.S. Cl.  
CPC ........... *A61B 8/5207* (2013.01); *A61B 8/0866* (2013.01); *A61B 8/4405* (2013.01); *A61B 8/465* (2013.01); *A61B 8/483* (2013.01)

(58) Field of Classification Search  
None  
See application file for complete search history.

(56) References Cited

U.S. PATENT DOCUMENTS

| | | | |
|---|---|---|---|
| 4,333,345 A * | 6/1982 | Renzel et al. | 73/606 |
| 2006/0093198 A1* | 5/2006 | Fram et al. | 382/128 |
| 2008/0146932 A1* | 6/2008 | Chalana et al. | 600/447 |
| 2009/0099449 A1* | 4/2009 | Lundberg | 600/443 |
| 2009/0153472 A1* | 6/2009 | Bloem et al. | 345/156 |
| 2009/0285464 A1* | 11/2009 | Urushiya | 382/131 |
| 2010/0179427 A1 | 7/2010 | Yamamoto | |
| 2011/0301441 A1* | 12/2011 | Bandic et al. | 600/306 |
| 2014/0243670 A1* | 8/2014 | Smillie et al. | 600/443 |

FOREIGN PATENT DOCUMENTS

| | | |
|---|---|---|
| CN | 101721227 A | 6/2010 |
| JP | 2006-000127 | 1/2006 |
| JP | 2006-23820 | 1/2006 |
| JP | 2006-102353 | 4/2006 |
| JP | 2006-122722 | 5/2006 |
| JP | 2007-075158 | 3/2007 |
| JP | 2011-149366 | 8/2011 |

OTHER PUBLICATIONS

GE Healthcare, Voluson™ E8/E8 Expert Basic User Manual Revision 2, Jan. 2013.*

(Continued)

*Primary Examiner* — Matthew Bella  
*Assistant Examiner* — Soo Shin  
(74) *Attorney, Agent, or Firm* — Oblon, McClelland, Maier & Neustadt, L.L.P.

(57) ABSTRACT

A medical imaging data processing apparatus comprising a data receiving unit for receiving imaging data, a rendering unit for rendering images from the imaging data according to one or more rendering parameters and a selection unit configured to output a plurality of images rendered by the rendering unit. At least one of the plurality of output images is rendered using one or more rendering parameter having a value that is different to the value used to render one or more of the other rendered images. The output images are selectable to select the value of one or more rendering parameters associated with the selected image.

20 Claims, 5 Drawing Sheets

(56) References Cited

OTHER PUBLICATIONS

Magnus Wahrenberg, "Volume Rendering for 3D Display," MS Thesis, Royal Institute of Technology, KTH Computer Science and Communication, Stockholm, Sweden 2006.*

GE Healthcare Voluson E8 ultrasound demonstration, YouTube Video uploaded on Dec. 21, 2011. Video Link: https://www.youtube.com/watch?v=cl6Ae1Flukg.*

J. Marks, et al., "Design Galleries: A general approach to setting parameters for computer graphics and animation", In Proceedings SIGGRAPH 97, Http://nrs.harvard.edu/urn-3:HUL.InstRepos:2265285; 1997, pp. 389-400.

Combined Chinese Office Action and Search Report issued on Mar. 14, 2016 in Patent Application No. 201410181404.5 (with English language translation of categories of cited documents).

* cited by examiner

MEDICAL IMAGING DATA PROCESSING APPARATUS AND METHOD

FIELD

Embodiments described herein relate generally to medical image data processing apparatus and methods, such as apparatus and methods that provide for the varying of parameters used in rendering of images obtained using medical imaging systems.

BACKGROUND

The generation of 3D/4D volume rendered images from data collected by medical imaging devices has become increasing popular as a method for improving medical visualisation. Such techniques can be applicable to a variety of medical imaging methods such as, but not limited to, ultrasound imaging, MRI, CT, PET and the like.

For example, ultrasound scanning that uses transmission and reception of sound waves from a transducer can be used to image structures inside the body. The imaging of a fetus within the womb is a well-known example of the use of this technique.

Three-dimensional (3D) ultrasound images can be generated by using software to combine ultrasound data that has been taken at different positions or angles, and to render an image from the combined data using methods such as simple surface shading or direct volume rendering. In four-dimensional (4D) ultrasound imaging systems, a series of three-dimensional images obtained at different times is dynamically rendered to produce a moving 3D image, for example, a 3D ultrasound movie.

In recent years, 3D and 4D ultrasound images have been made more photorealistic through the use of advanced lighting and rendering techniques (such as global illumination, gradient free lighting, subsurface scattering or photon mapping) that simulate illumination of the imaged object from a particular angle.

Selection of optimal rendering parameters, such as light position, colour map, brightness, radiosity, and the like, can have a significant impact on the quality and realism of the rendered images derived from the data collected by the medical imaging devices. However, many operators of medical imaging devices do not have the time or expertise in rendering techniques to explore and select the optimal rendering parameters for a particular imaging situation and the interfaces of some medical imaging systems may not be as intuitive as users would like.

BRIEF DESCRIPTION OF THE DRAWINGS

Embodiments are now described, by way of non-limiting example, and are illustrated in the following figures, in which.

DETAILED DESCRIPTION

According to an embodiment there is provided an imaging data processing apparatus, the imaging data processing apparatus comprising a data receiving unit for receiving imaging data; a rendering unit for rendering images from the imaging data according to one or more rendering parameters; and a selection unit configured to output a plurality of images rendered by the rendering unit, wherein at least one and preferably each of the plurality of output images is rendered using a value of at least one rendering parameter that is different to the value used to render at least one and preferably each of the other rendered images, wherein the images are selectable to select the one or more rendering parameters associated with the selected image.

In particular embodiments, the selection unit is configured to receive user input from one of more user input devices and provide output to one or more displays. The selection unit is operable to output the plurality of rendered images of the imaged objects for simultaneous display. The selection unit is configured to allow a user to make an input indicative of a selected rendered image from the plurality of rendered images in order to select the at least one rendering parameter used to render the selected image for subsequent use by the rendering unit.

Figure 1:
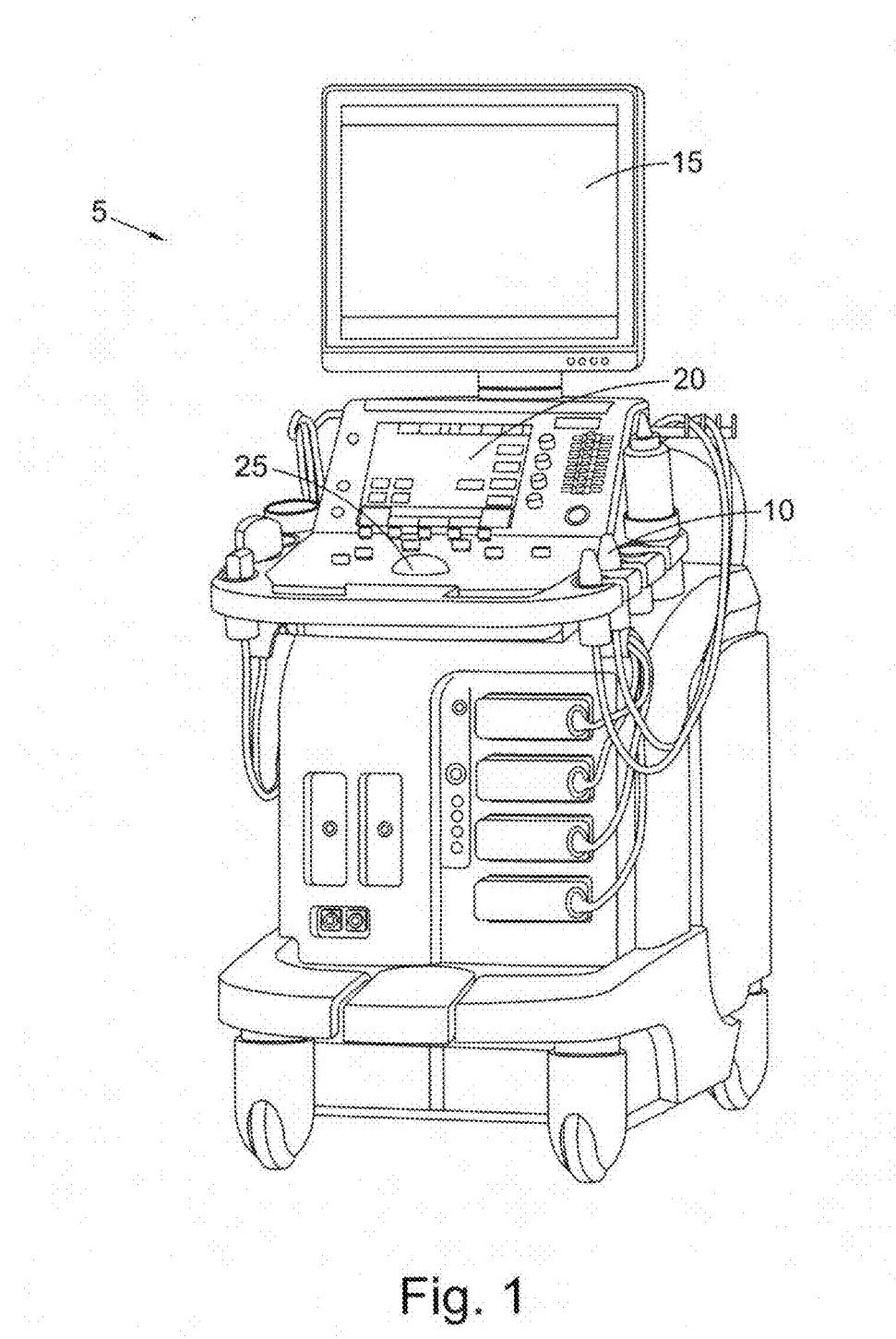
FIG. 1 shows a medical imaging device according to an embodiment of the invention.
Figure 2:
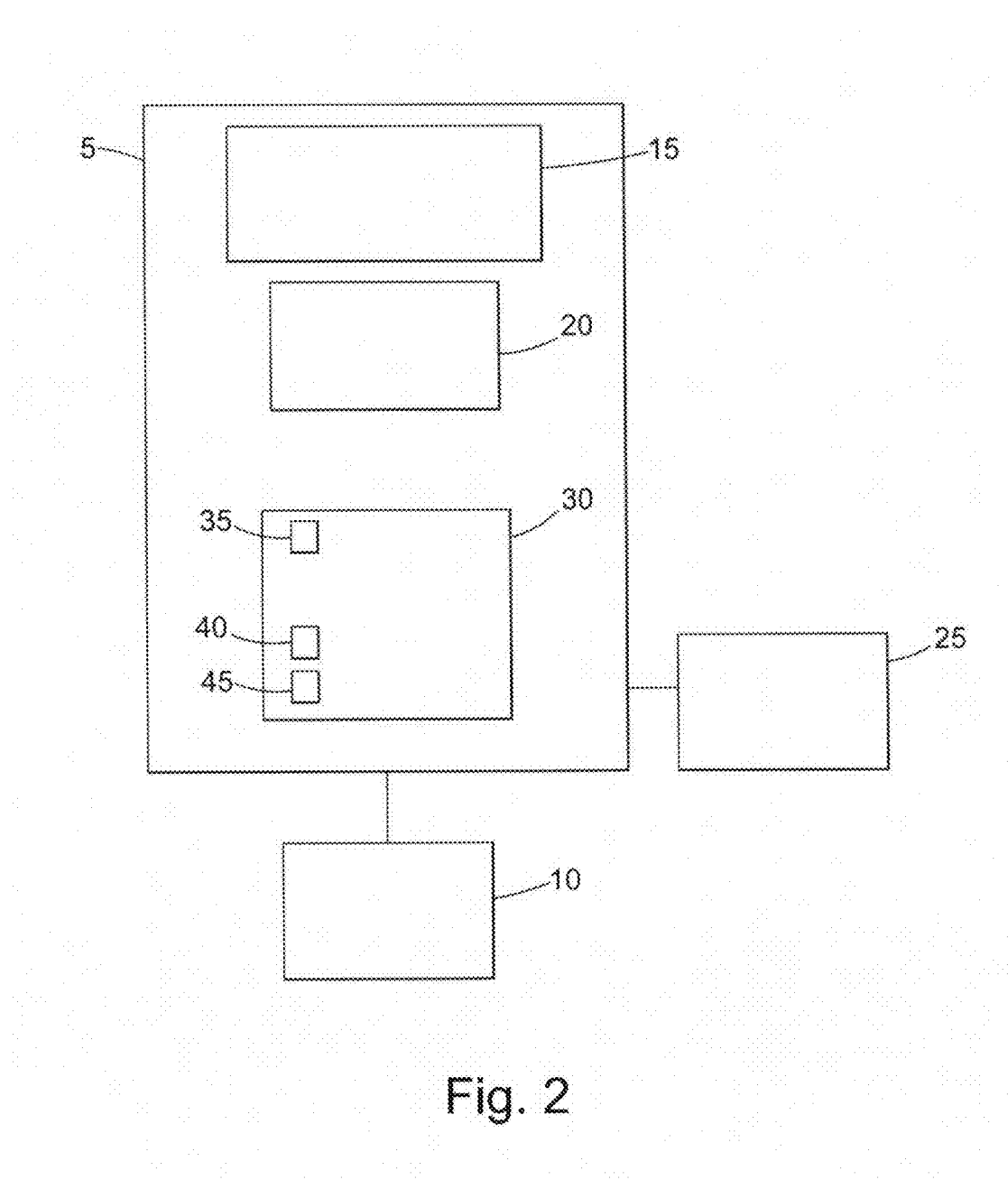
FIG. 2 is a schematic diagram of the medical imaging device of FIG. 1.

A medical image processing apparatus according to a first embodiment, which in this particular example is configured to produce an ultrasound image, is illustrated in FIGS. 1 and 2. The apparatus comprises an ultrasound scanner 5 and associated ultrasound measurement probe 10. The ultrasound scanner 5 has a hardware specification similar to the Toshiba Aplio 500 and the measurement probe 10 comprises a volume imaging ultrasound transducer such as the Toshiba PVT-375MV. However, it will be appreciated that any other suitable 3D and/or 4D imaging ultrasound system or machine could be used.

The ultrasound machine 5 comprises a main display screen 15 for displaying an ultrasound image and a control screen 20 forming part of a control panel. In this particular embodiment, the control screen 20 is a touch screen such that it operates both as a user input device and an output device for presenting information and images to the user. Although a touch screen is preferable for user input and output, it will be appreciated that other arrangements could be used, such as a non-touch screen in conjunction with one or more user input devices known in the art such as a trackball, a keyboard, a joystick, a mouse and the like. Furthermore, it will be appreciated that more than one user input and/or output device may be provided. For example, the touch control screen 20 may be provided along with at least one other input device 25 such as a trackball, keyboard, joystick, and/or mouse.

In addition, in a further embodiment, one or more of the input or output devices 20, 25 need not form part of the ultrasound machine 5. For example, they can be separate devices that are connectable by cable to the ultrasound machine 5, or can otherwise communicate with the ultrasound machine 5 such as by wireless and/or network communication. Furthermore, although a separate main display screen 15 and control screen 20 are advantageously provided, it will be appreciated that it is also possible to provide a single screen that is operable as both the main display screen 15 and the control screen 20.

The ultrasound machine 5 comprises processing apparatus 30 for processing data, including imaging data generated using the measurement probe 10. The processing apparatus 30 includes one or more components such as a hard drive, RAM, ROM, a data bus, an operating system including various device drivers, and hardware devices including a graphics card. Such components are not shown in FIG. 2 for clarity. In an alternative embodiment, the processing apparatus 30 is not part of the ultrasound machine 5 and is, for example, a personal computer.

The processing apparatus 30 also includes a data receiving unit 35 for receiving volume data. In the present embodiment, the data receiving unit 35 receives volume data collected using the ultrasound measurement probe 10, wherein the imaging data comprises ultrasound data representative of at least part of one or more subjects or objects that are located in an imaging volume that is being or has been imaged using the measurement probe 10. For example, the imaging data may be collected from the imaging of a fetus in a mother's womb, or of an organ of the body such as a heart, pancreas, liver, gall bladder, bile duct, kidney, spleen or bladder, and/or of an instrument or other apparatus, such as a needle, within a body. It will be appreciated that the imaging data can be received and/or processed in real time or received from a suitable data store for processing at a suitable time.

The processing apparatus 30 further comprises a rendering unit 40 for rendering images of the imaged subjects or objects represented by the imaging data according to one or more rendering parameters. The rendering unit 40 uses the imaging data to render a more photorealistic image from the imaging data using rendering techniques known in the art. The rendering process used by the rendering unit 40 uses the one or more rendering parameters, such as a virtual light position, colour map, texture, radiosity, brightness and/or the like, which can be selected and optimised, for example, to produce the clearest or most photorealistic image. Suitable rendering techniques and the rendering parameters used thereby are well known in the art.

Whilst use of the rendering unit can potentially provide more realistic images and/or allow greater differentiation between subjects and objects represented by the imaging data, it is generally necessary to determine the optimal or suitable rendering parameters to achieve the best rendered image.

For example, one technique to allow selection of rendering parameters is to present a real time image rendered from the imaging data on the main display screen 15 and to allow the user to vary one or more of the rendering parameters, such as a virtual light position relative to the imaged object(s), using one of the input devices 25 such as a trackball. As the user operates the input device 25, the rendering parameter(s) and the resultant rendered image that is displayed on the main display screen 15 are varied accordingly. However, this process can be time consuming and computationally intensive while the user scans through the rendering parameter space using the input device 25 in order to produce an optimal rendered image. This process can also require a high level of user experience and expertise to home in on the optimal rendering parameters.

Another option for selecting the rendering parameters is the use of preset rendering parameters. In this way, the user can be presented with a variety of preset options, for example on the control screen 20, from which the user can select. For example, in certain embodiments each of the presets are represented by a written description of the rendering parameter value represented by the preset or by a generic image that represents the preset, for example a series of thumbnails showing the position of the virtual light source relative to the imaging volume or object.

Figure 3:
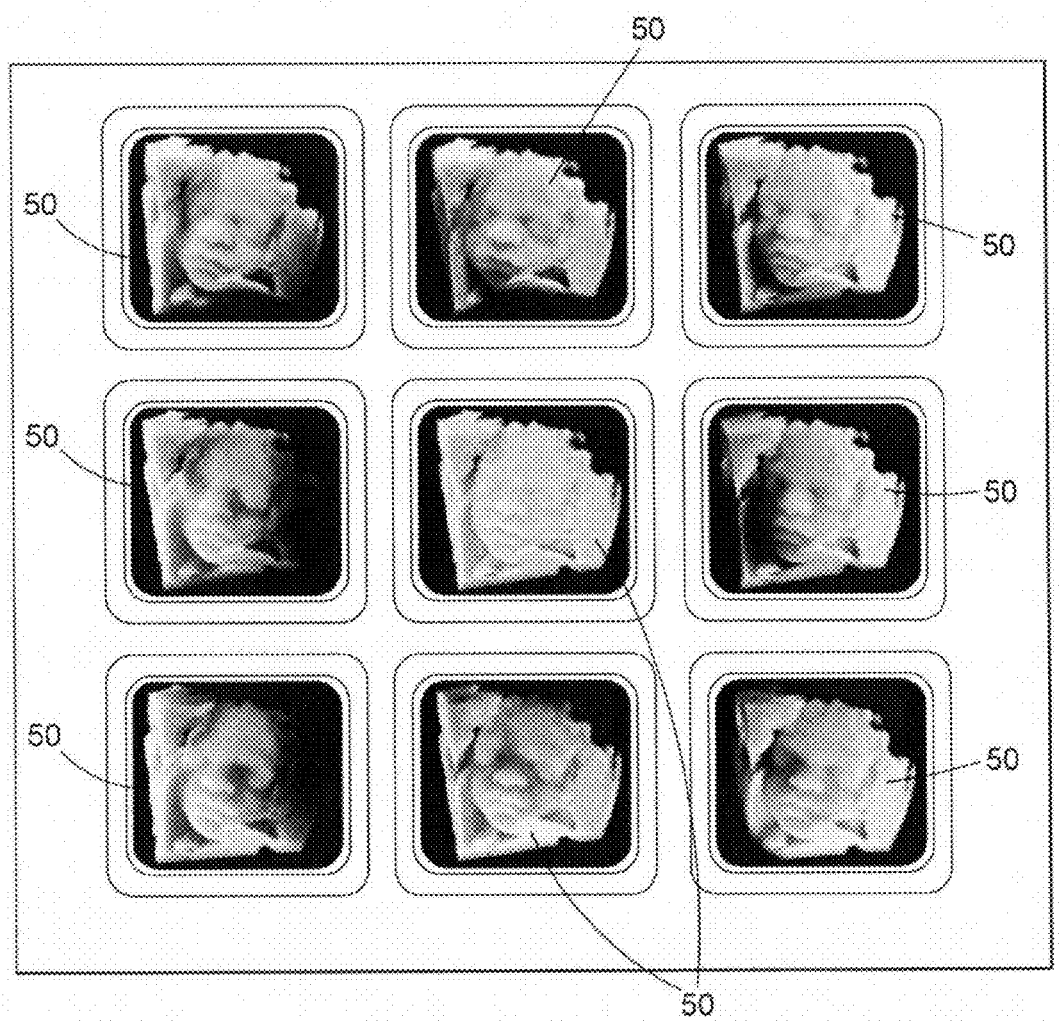
FIG. 3 is an illustration of a user interface for selecting a rendering parameter for use in rendering an image in accordance an embodiment of the invention.

In particularly advantageous embodiments, the processing apparatus 30 comprises a selection unit 45 that causes the control screen 20 to display a user selection interface that comprises a plurality of simultaneously displayed output images in the form of thumbnail images 50, each thumbnail image 50 comprising a rendered image based on the same imaging data, as shown in FIG. 3. Each thumbnail image 50 is rendered using a value of at least one rendering parameter that is different to the values used to render each of the other thumbnail images 50. In embodiments, the value of the at least one rendering parameter used to render each thumbnail image 50 comprises a preset value of the at least one rendering parameter or a value within a preset range of values of the at least one rendering parameter. For example, in the case of the rendering parameters comprising a virtual light position, each thumbnail image 50 shows an image rendered from the same imaging data but using a different virtual light position based on preset values, such as in the example shown in FIG. 3.

The user can then select which value(s) of the at least one rendering parameter gives the best image by simply identifying which of the presented thumbnail images 50 is most acceptable to the user. The user can make their selection, for example, by pressing on the preferred thumbnail image 50 on the touch screen 20 (thus the thumbnail image may act as a virtual button) or by selecting the thumbnail image 50 using a pointer moved by a mouse or trackball or by selecting a key or button associated with the desired thumbnail image 50. When the user selects a thumbnail image 50 then the value(s) of the at least one rendering parameter used to render the selected thumbnail image 50 becomes the default value(s) for the at least one rendering parameter for use by the rendering unit 40 in subsequently rendering images for display on the main display screen 15.

Whilst the rendering parameters that can be selected by the user are described as presets, it will be appreciated that the preset values of the rendering parameter may be set by the manufacturer or supplier during manufacture and/or by subsequent update, or set by a user or determined by the processing apparatus. The rendering parameters can, for example, be set to cover or provide an even spread of values over a certain range of the rendering parameter.

The thumbnail images 50 in certain embodiments is rendered based on the currently or most recently collected imaging data, such that the thumbnail images 50 are updated in real time. The thumbnail images may thus be live replicas of the main screen. However, in certain circumstances, this could be computationally demanding and may produce distracting peripheral motion as the user interacts with the main screen 15. According to embodiments, the thumbnail images 50 remain static and are only updated periodically or when certain conditions are met, such as when user interaction with the ultrasound machine 5 (for example by using features such as rotation, 4D cine and/or thresholding) is determined to have ceased and/or the utilisation of the processing apparatus 30 by other processes is below a certain level.

Any suitable technique for determining when user interaction has ceased can be used. In some embodiments, the selection unit 45 is configured to monitor the time that has elapsed since the last interaction of the user with user input devices of the ultrasound machine, for example one or more of the input buttons, knobs, keyboard, mouse or trackball. If the elapsed time is greater than a threshold time, the selection unit 45 determines that user interaction has ceased and updates the thumbnail images 50. Additionally or alternatively, in embodiments, the selection unit 45 monitors the movement of the measurement probe 4, or movement of images obtained from measurements by the measurement probe 4, and determines that the user interaction has ceased when the amount or speed of movement is below a threshold value for a threshold period of time.

Figure 4:
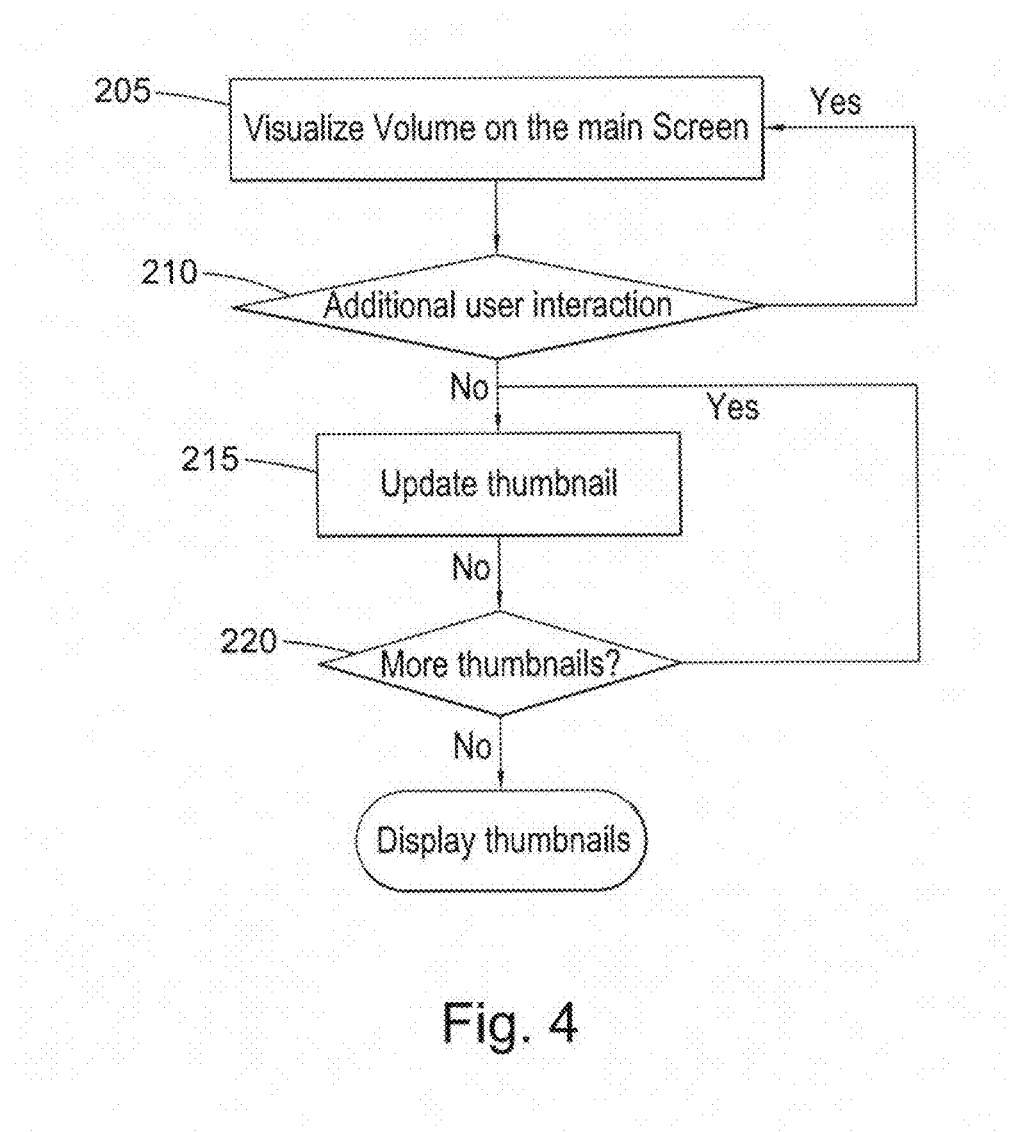
FIG. 4 is a flow chart illustrating a method of updating the user interface of the embodiment of FIG. 3.

The system of FIG. 2 is configured to perform a process of updating the thumbnail image 50 having a series of stages as illustrated in overview in the flowchart of FIG. 4.

Figure 5:
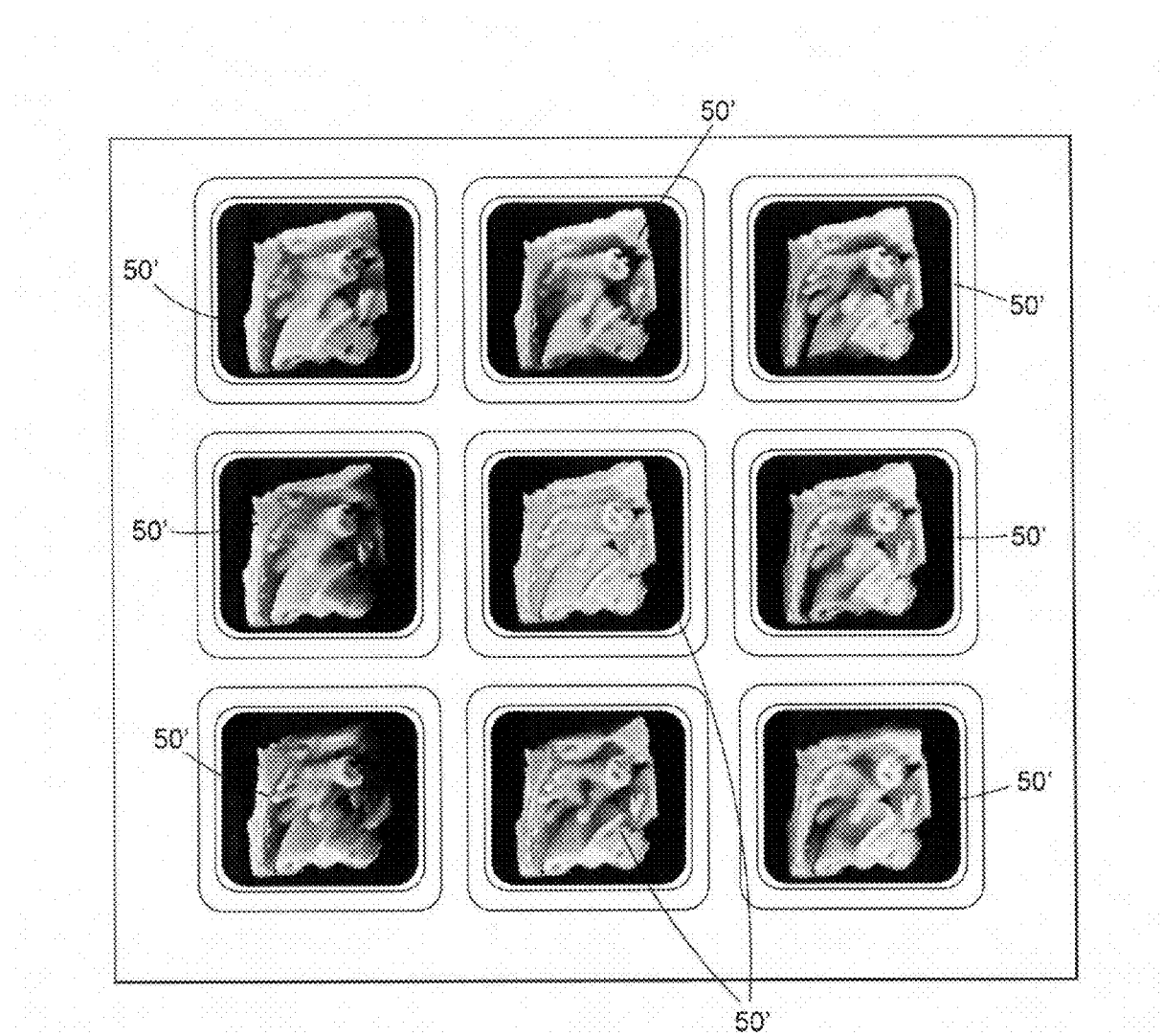
FIG. 5 is an illustration of the user interface of FIG. 3 in which has been re-rendered to reflect a different imaged volume.

At the first stage 205, an image of the imaged volume derived from the imaging data is presented on the main screen 15 wherein, if the presented image is a rendered image, then pre-set, current or pre-existing rendering parameters are used to generate the rendered image from the imaging data. At stage 210, the user can then interact with the ultrasound machine 5 in the normal manner, for example by moving the measurement probe 10 to select a desired imaging volume and to use functions of the ultrasound machine 5 such as rotation, 4D cine and thresholding. While it is determined that the user is currently interacting with the ultrasound machine 5, the image presented on the main screen 15 is updated as required in the conventional manner. When it is determined that the user interaction has stopped, the thumbnail image 50 are each updated with the current or latest imaging data in place of the imaging data that was used to form the thumbnail images 50 before the detected user interaction at stage 215. At step 220, the thumbnail updating step is repeated until each of the thumbnails have been updated with the current or latest imaging data, an example of updated thumbnail images 50' being shown in FIG. 5. In this instance, whilst the imaging data is updated, the rendering parameters of each of the presets that are used to generate each associated thumbnail image 50, 50' remain the same.

In an alternative embodiment, the data receiving unit is configured to determine how much image change has been caused, for example, by the user interaction and updates the thumbnail images or other output images only when the amount of image change is larger than a predetermined threshold. That can ensure that there is a limitation of the processing load needed to generate the thumbnail images. The amount of image change can be determined using any suitable technique, for example using a Sum of Absolute Difference (SAD) technique. In such a SAD technique, the absolute difference is calculated by summing the difference for each pixel between the latest image and the previous image. If the absolute difference value is greater than the predetermined threshold the thumbnail images are updated.

In an embodiment, the selection unit 45 is configured to provide selection of rendering parameters in a hierarchical manner, where a user can drill down through a hierarchical series of parameter selection user interfaces to allow successive fine tuning of the values of the one or more rendering parameter(s). In this case, when the user selects one of the presets, then a new user interface containing a plurality of thumbnail images 50, 50' representing a narrower range of rendering parameter values than the previous user interface is displayed. The rendering parameter value(s) of the new parameter selection user interface that are used to generate each of the thumbnail images 50, 50' are within a set range of the rendering parameter value(s) associated with the previously selected thumbnail image. The range of the rendering parameter value(s) of the new user interface can be within a range bounded by half of the difference between the value of the rendering parameter(s) associated with the previously selected thumbnail image/preset and that of the next closest thumbnail images/presets that the user could have selected in the previous user interface. It will be appreciated that the selection unit 45 may provide further user interfaces in the hierarchy to provide any required level of sensitivity of the rendering parameter selection process.

Additionally or alternatively to the above hierarchical method for providing sensitive tuning of the rendering parameter(s), the value of rendering parameters can be selected using a composite input method, wherein both selection of presets using rendered thumbnail images, as detailed above, and also variation of the values of the one or more rendering parameters using another user input device 25 or method can be used to select the value of a rendering parameter. Advantageously, one method or user input device, such as the selection of presets as described above, can be used to select an approximate value or range of the rendering parameter and a second input device 25, such as a trackball or mouse, can be used to fine tune the value of the rendering parameter within the selected range or about the selected approximate value.

In this way, the provision of presets reduces the rendering parameter space that needs to be explored using the other input device 25. This can allow use of input devices 25, such as a trackball or mouse, that provide a high degree of accuracy in selecting the value of the rendering parameter whilst at the same time reducing the time required to select the desired value of the rendering parameter by quickly and intuitively reducing the parameter space to be explored through the use of presets represented by rendered thumbnail images 50, 50' on the control screen 20.

In some such embodiments, in response to selection of a preset causing display of a new user interface containing a plurality of thumbnail images 50, 50' representing a narrower range of rendering parameter values, the selection unit automatically decreases the range of values of the rendering parameter that can subsequently be selected using the second input device, by restricting the maximum and minimum values of the parameter that can be selected using that second input device.

Beneficially, in some embodiments, the sensitivity of the other input device 25, such as the trackball or mouse, can be automatically altered when a preset is selected from the control screen. For example, in some embodiments, the amount of change in the value of the rendering parameter for a given amount of movement of the input device 25 is decreased, when a preset is selected from the control screen 20. This further improves the ease of selecting the desired input parameter.

In an embodiment, the above techniques can be used to select values for more than one rendering parameter. For example, the selection unit 45 can allow the user to switch between user interfaces, wherein the value of a different rendering parameter is varied in each user interface in order to produce the thumbnail images 50, 50'. Examples of differing rendering parameters that could be varied in this way include virtual light position, colour map, radiosity, brightness, texture and the like. The value of any of the rendering parameters can then be selected as described above.

According to embodiments, the thumbnail images 50, 50' can be displayed in various patterns or arrangements, such as in a grid, in a loop or circle, in a linear arrangement or in a non-uniform arrangement. Advantageously, the image thumbnails 50, 50' can be arranged in a way that is representative of the property or value of the rendering parameter that they represent, particularly when the property represents a position. For example, if a thumbnail image 50, 50' represents the position of a virtual light source to the left of the imaged object, then that thumbnail image 50, 50' can be provided to the left of the control screen 20, a thumbnail image 50, 50' representing the position of a virtual light source above or behind the imaged object can be positioned at the top of the control screen 20 and so on, such that the position of the thumbnail image 50, 50' on the control screen 20 is indicative of the position of the virtual light source relative to the imaged object. In another example, the thumbnail images 50, 50' represent brightness and the thumbnail images 50, 50' are arranged linearly, with the thumbnail image 50, 50' representing the highest brightness being provided at the top of the control screen 20 with successively lower thumbnail images 50, 50' representing successively lower brightness values.

In certain embodiments functionality is provided by way of a computer program having computer-readable instructions that are executable to perform the method of the embodiments. However, functionality may be provided by software, hardware or any suitable combination of hardware and software. In some embodiments, the various units may be implemented as one or more ASICs (application specific integrated circuit) or FPGAs (field programmable gate array).

Whilst particular units have been described herein, in alternative embodiments, functionality of one or more of those units can be provided by a single unit, processing resource or other component, or functionality provided by a single unit can be provided by two or more units or other components in combination. Reference to a single unit encompasses multiple components providing the functionality of that unit, whether or not such components are remote from one another, and reference to multiple units encompasses a single component providing the functionality of those units.

While certain embodiments have been described, these embodiments have been presented by way of example only, and are not intended to limit the scope of the inventions. Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical imaging data processing apparatus comprising:
   circuitry configured to
      receive volume data, and
      generate rendering images by rendering the volume data according to rendering parameter sets, each of the rendering parameter sets including a virtual light position being different with respect to each of the rendering parameter sets; and
   a display configured to display thumbnail images of the rendering images depicting the virtual light positions, wherein
   one of the thumbnail images is selected according to a user instruction, and
   the display is configured to display a rendering image corresponding to the selected thumbnail image after the user instruction.

2. The apparatus according to claim 1, wherein the values of the rendering parameter sets used to generate the rendering images are preset values.

3. The apparatus according to claim 1, wherein the at least one rendering parameter set further comprises at least one of a colour map, radiosity, brightness, and texture.

4. The apparatus according to claim 1, wherein
   the medical imaging data processing apparatus comprises or is comprised in an ultrasound scanner,
   the ultrasound scanner comprises a control screen in the form of a touchscreen,
   the display comprises the touchscreen,
   the display displays the plurality of thumbnail images on the touchscreen, and the selection of the virtual light position from the volume data is performed by selecting one of the thumbnail images using the touchscreen, and
   the circuitry, in response to the selection of the virtual light position from the volume data using the touchscreen, generates the rendering image.

5. The apparatus according to claim 1, wherein the location of each of the plurality of thumbnail images when displayed is indicative of the value of at least one of the one or more rendering parameter sets used to generate at least one of the rendering images.

6. The apparatus according to claim 3, wherein the display is configured to output a hierarchical series of user interfaces, wherein upon selection of a thumbnail image, the display is configured to display a plurality of thumbnail images representing a narrower range of rendering parameter values than the previous thumbnail images.

7. The apparatus according to claim 6, wherein the plurality of displayed thumbnail images are selectable using a first input device in order to select the value of at least one rendering parameter set and the value of the at least one rendering parameter set is also variable or selectable using at least a second input device.

8. The apparatus according to claim 1, wherein
   at least one of the plurality of thumbnail images is displayed using a value of the at least one rendering parameter set that is different to the value used to display at least one of the other displayed thumbnail images,
   the thumbnail images are selectable to select the value of the at least one rendering parameter set,
   the plurality of thumbnail images are selectable using a first input device in order to select the value of at least one rendering parameter set and the value of the at least one rendering parameter set is also variable or selectable using at least a second input device, and
   the display is configured such that when a thumbnail image is selected using the first input device, the display automatically increases sensitivity of the second input device so as to automatically decrease the amount of change in the value of the rendering parameter set for a given amount of movement of the second input device.

9. The apparatus according to claim 8, wherein the first input device is a touch screen and the second input device comprises at least one of a trackball, a joystick, and a mouse.

10. The apparatus according to claim 1, wherein the circuitry measures amount of change in at least one image parameter set and the thumbnail images are updated when the amount of change is larger than a predetermined threshold.

11. The apparatus according to claim 1, wherein the thumbnail images are updated depending on positions of an ultrasound scanner.

12. A method of processing medical imaging data, the method comprising:

receiving volume data;

generating rendering images by rendering the volume data according to rendering parameter sets, each of the rendering parameter sets including a virtual light position being different with respect to each of the rendering parameter sets;

displaying thumbnail images of the rendering images depicting the virtual light positions, one of the thumbnail images being selected according to a user instruction; and displaying a rendering image corresponding to the selected thumbnail image after the user instruction.

13. The method according to claim 12, wherein the values of the rendering parameter sets used to generate the rendering images are preset values.

14. The method according to claim 12, wherein the at least one rendering parameter set further comprises at least one of a colour map, radiosity, brightness, and texture.

15. The method according to claim 12, further comprising outputting a hierarchical series of user interfaces and, upon selection of a thumbnail image, displaying a plurality of thumbnail images representing a narrower range of rendering parameter set values than the previous thumbnail images.

16. The method according to claim 12, further comprising selecting the plurality of thumbnail images using a first input device in order to select the value of one or more rendering parameter sets and also varying or selecting the value of the one or more rendering parameter sets using at least a second input device.

17. The method according to claim 16, further comprising at least one of
- automatically increasing the sensitivity of the second input device; and
- automatically decreasing the amount of change in the value of the rendering parameter set for a given amount of movement of the second input device, when a thumbnail image is selected using the first input device.

18. The method according to claim 17, wherein the first input device is a touch screen and the second input device comprises at least one of a trackball, a joystick and a mouse.

19. The method according to claim 12, further comprising at least one of a) and b):
- a) updating the thumbnail images when user interaction with an apparatus for at least one of collecting and visualizing the volume data ceases; and
- b) updating the thumbnail images periodically.

20. A non-transitory memory storing computer-readable instructions that are executable to perform a method according to claim 12.

* * * * *